United States Patent [19]

Tang et al.

[11] Patent Number: 5,256,572
[45] Date of Patent: Oct. 26, 1993

[54] METHOD FOR DETERMINING RESIDUAL OIL SATURATION OF A WATERED-OUT RESERVOIR

[75] Inventors: Joseph S. Tang; Kelvin N. Wood; Harold G. Taylor, all of Calgary, Canada

[73] Assignee: Exxon Production Research Company, Houston, Tex.

[21] Appl. No.: 711,285

[22] Filed: Jun. 6, 1991

[51] Int. Cl.$^5$ ............. G01N 33/24; G01N 33/26
[52] U.S. Cl. ............................ 436/27; 166/250; 166/252; 436/28; 436/29; 436/56; 436/57
[58] Field of Search ............ 166/250, 252; 436/27, 436/28, 29, 56, 57

[56] References Cited

U.S. PATENT DOCUMENTS

| | | | |
|---|---|---|---|
| 3,008,521 | 11/1961 | Boucher | 166/250 |
| 3,231,018 | 1/1966 | Handy | 166/252 |
| 3,333,631 | 8/1967 | Heller | 166/252 |
| 3,690,167 | 9/1972 | Chase, Jr. et al. | 436/27 X |
| 3,847,548 | 11/1974 | Keller et al. | 166/252 X |
| 3,894,584 | 7/1975 | Feril | 166/252 X |
| 4,223,727 | 9/1980 | Suster, Jr. et al. | 166/250 |
| 4,725,551 | 2/1988 | Thompson | 436/56 X |
| 4,742,873 | 5/1988 | Craig, III | 166/252 |
| 4,782,898 | 11/1988 | Wellington et al. | 436/27 X |
| 5,111,882 | 5/1992 | Tang et al. | 436/27 X |

Primary Examiner—Jill A. Johnston
Attorney, Agent, or Firm—Pravel, Gambrell, Hewitt, Kimball and Krieger

[57] ABSTRACT

A method for determining residual oil saturation of a watered-out reservoir using two water soluble tracers having different partition coefficients in oil. The partitioning tracers are selected from the group consisting of tritiated or carbon 14 tagged alcohols, ketones, aldehydes, water and oil insoluble inorganics and organic radioactive isotopes. The tracers are injected into the formation, and their production curves are analyzed over a period of time to determine chromatographic separation of the tracers.

8 Claims, 5 Drawing Sheets

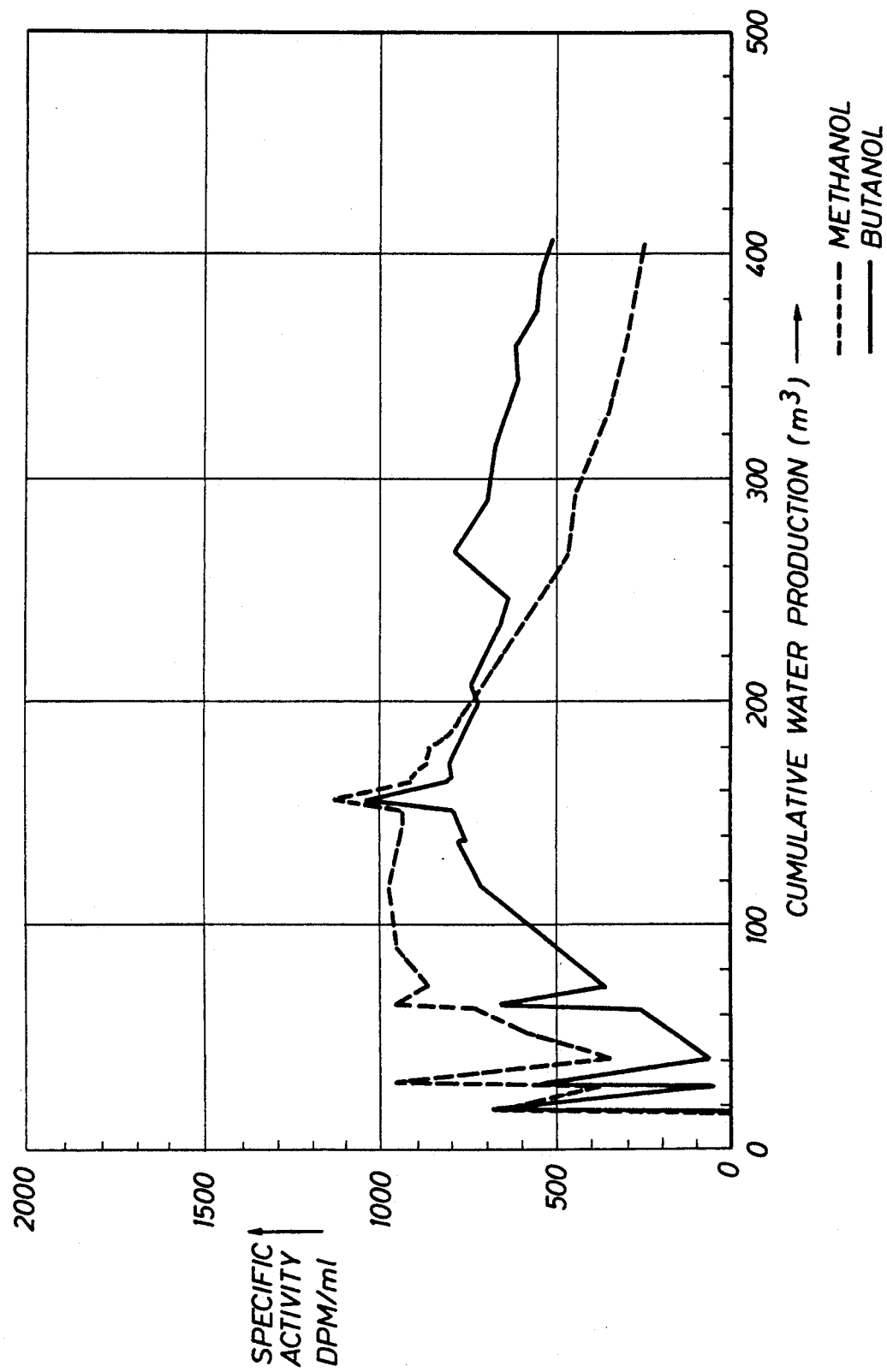

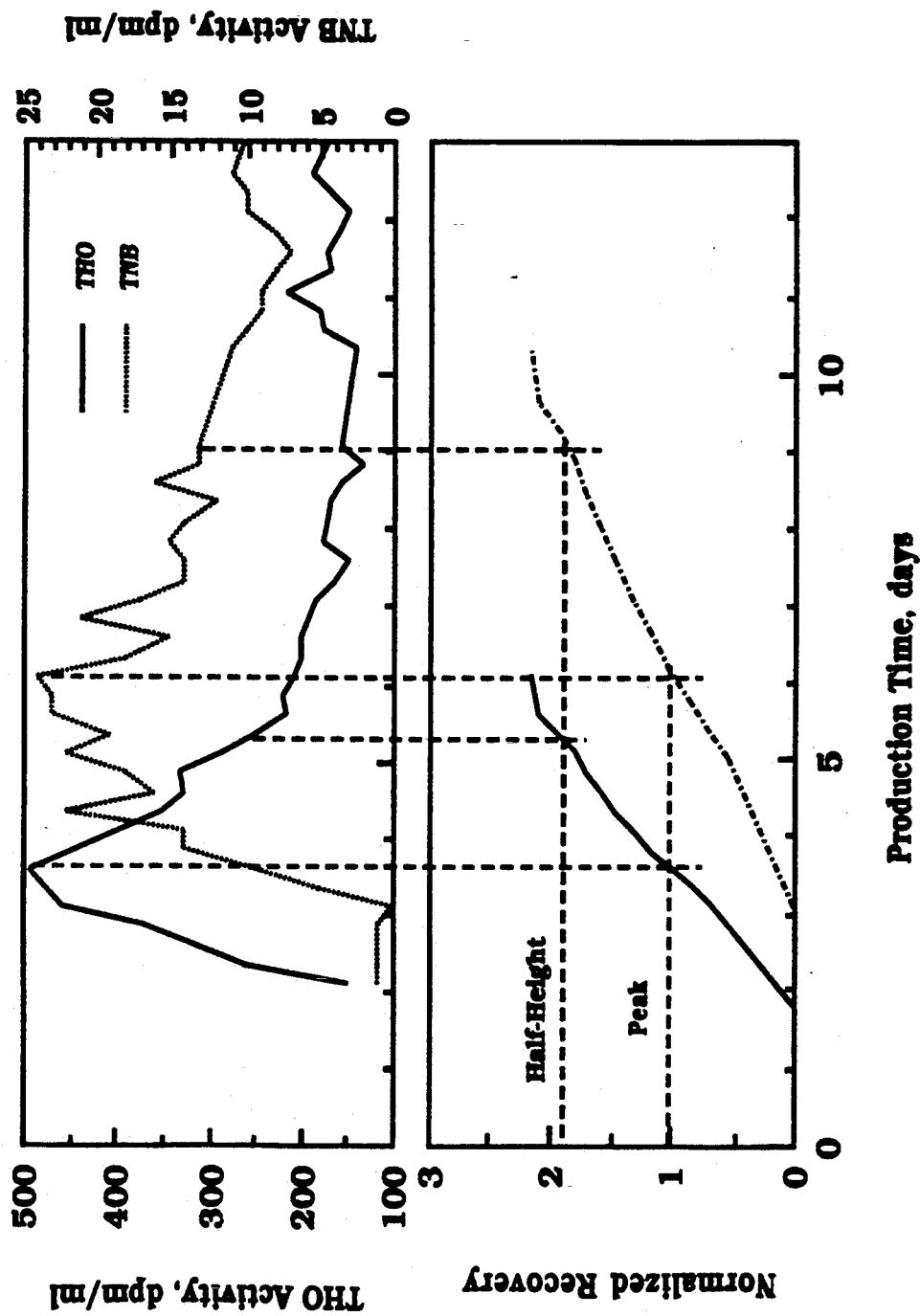
Figure 2. IWT-1 Normalized Recovery-Profile Crossplot

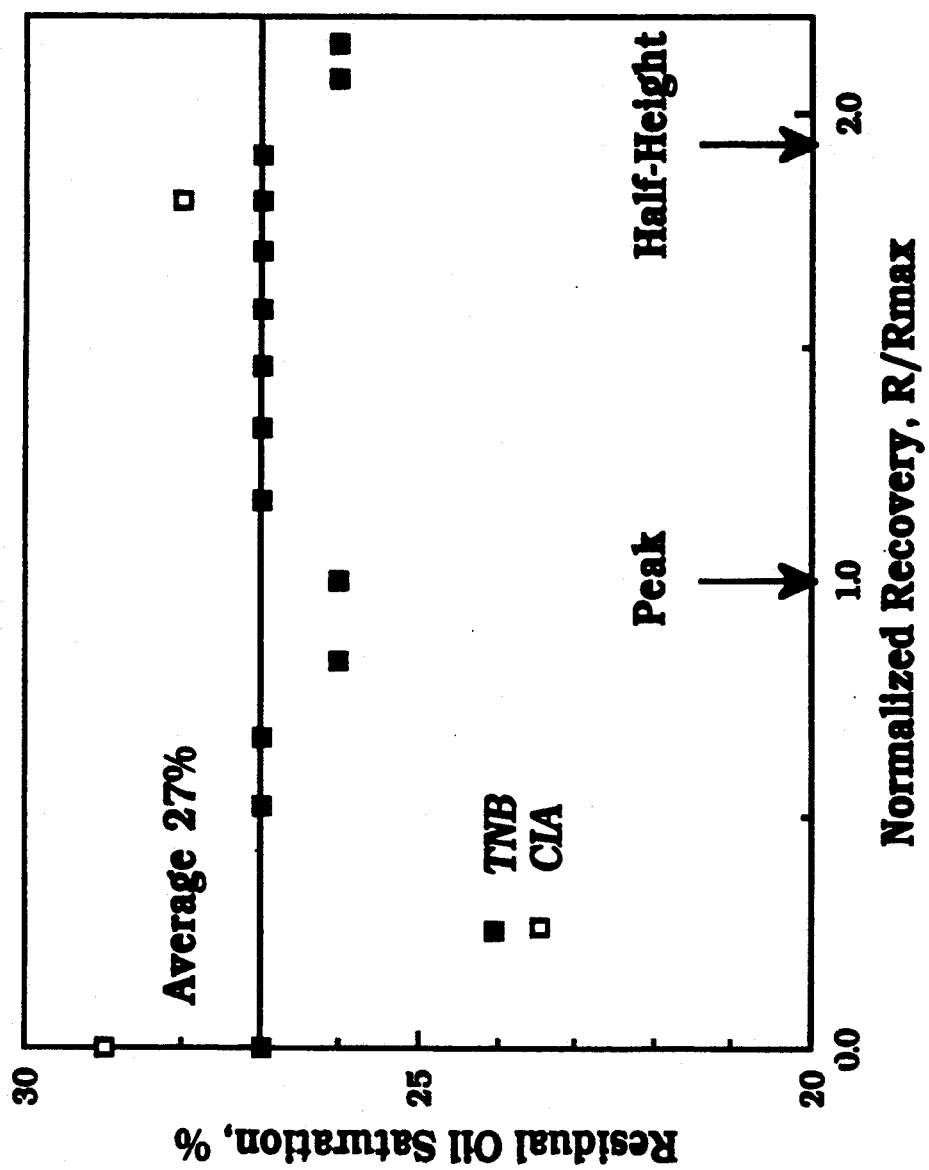
Figure 3. IWT-1 Sorw vs Normalized Recovery Plot

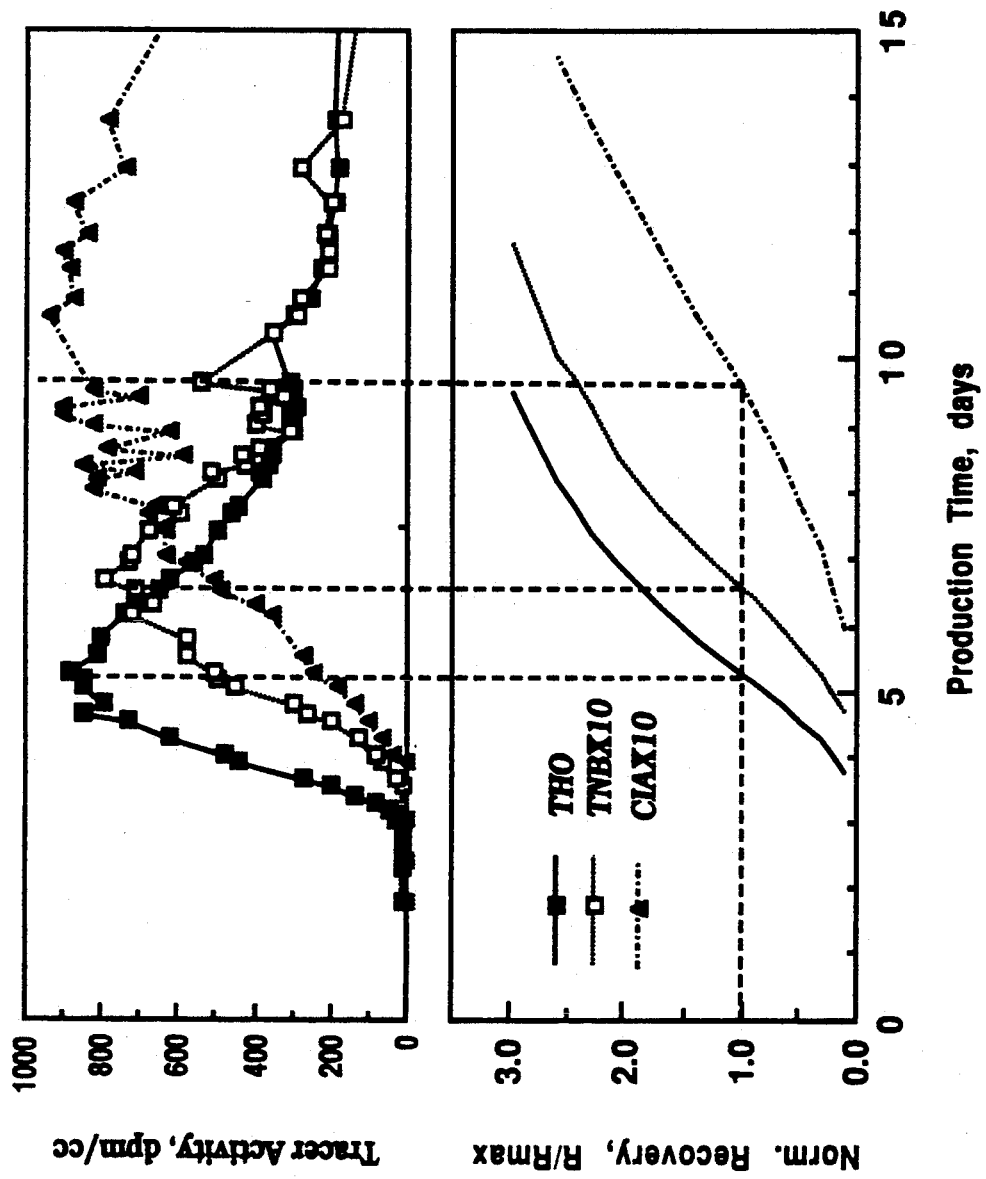

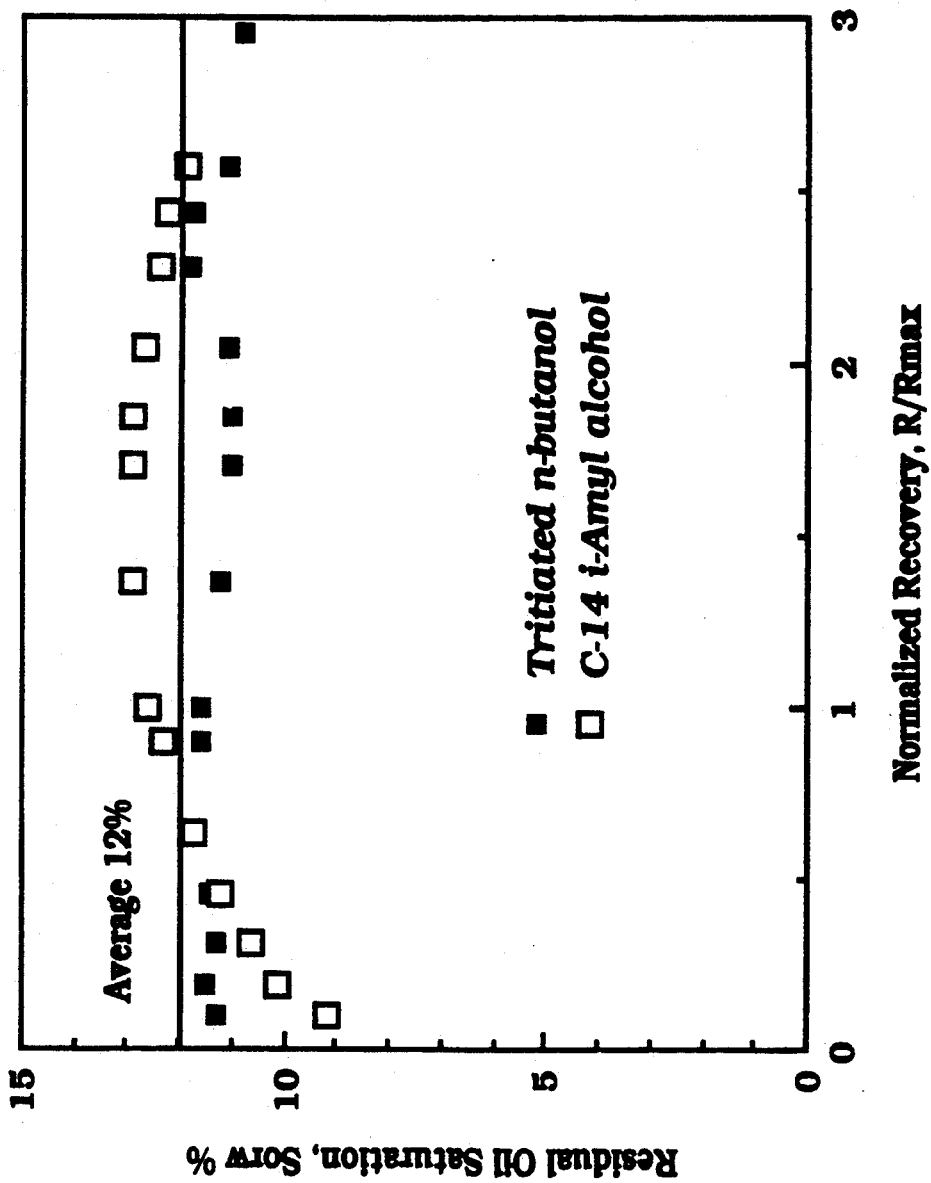

METHOD FOR DETERMINING RESIDUAL OIL SATURATION OF A WATERED-OUT RESERVOIR

FIELD OF THE INVENTION

The present invention relates to a method of using tracers to determine the in situ residual oil saturation between two locations in subterranean watered-out oil reservoirs. More specifically, the present invention relates to the determination of the relative concentrations of oil and water within subterranean reservoirs by measuring over a period of time the chromatographic separation of tracers having distinctly different partitioning coefficients in the oil and water phase fluids in the reservoir.

BACKGROUND OF THE INVENTION

Typical oil reservoir formations are made up of rock containing tiny, interconnected pore spaces which are saturated with oil, water, and gas. Knowledge of the concentrations of these fluids in the formation is critical for the efficient production of the oil. When the formation is first drilled, it is necessary to know the original oil saturation in order to plan the exploitation of the field. Later in the life of the field, the amount of oil remaining in the formation will often dictate the most efficient secondary and tertiary recovery operations. A particular need exists to determine the resident oil saturation of a watered-out formation following waterflooding.

Several methods are currently used to determine fluid saturations of a formation. One technique involves coring, i.e., direct sampling of the formation rock and fluids wherein a small portion of rock saturated with fluids is removed and brought to the surface where its fluid content can be analyzed. Coring, however, is susceptible to several shortcomings. First, the small sample may not be representative of the formation as a whole since it only investigates the immediate vicinity of the wellbore. Second, the coring process itself may change the fluid saturations of the samples. Finally, coring can usually only be done in newly drilled wells.

Another method of determining fluid saturations involves logging techniques. This method, too, suffers from the shortcoming of investigating a limited area which is in the immediate vicinity of the wellbore. In addition, logging techniques are often unable to differentiate between properties of the rock and those of its fluids.

Another approach involves material balance calculations based on production history. However, this approach is susceptible to error since it requires a knowledge of the initial fluid saturation of the formation by some other independent means.

More modern methods for determining fluid saturations involve the injection and production of tracers. The techniques are based on chromatographic theory. Typically, two tracers having different partition coefficients are used. The tracers are chromatographically retarded to different extents as they pass through the formation. The degree to which the two tracers are differentially retarded can be used to determine the formation fluid saturations. Tritiated water and water soluble forms of cesium and cobalt isotopes have gained wide acceptance as reliable water tracers for oil reservoir and groundwater studies.

Most tracer techniques for the determination of fluid saturations involve using a single well. A fundamental problem with single well testing is that only a very limited portion of the formation, the area immediately surrounding the wellbore, is investigated. Apart from this fundamental problem, single well testing which attempts to take advantage of chromatographic principles also suffers from an additional shortcoming—the "mirror image" effect. The mirror image effect occurs where two or more tracers having different partition coefficients are injected into a formation. The tracers will separate as they are injected into the formation, and the degree of separation will be a function of the oil saturation. However, when the tracers are withdrawn from the formation by means of the same well, the separation will disappear. In other words, when the tracers move away from the well, one tracer moves faster than the other due to the difference in partition coefficients and the residual oil saturation. When the well was placed on production, the faster moving tracer again moves further than the other and the two tracers arrive at the wellbore at approximately the same time.

Several schemes have been devised to avoid this problem. In one technique, the well is shut in for an extended period of time after the injection of the tracer. This allows the tracers to drift, i.e., to move in the formation under the influence of forces unrelated to the injection or withdrawal of fluids at the well. When the well is put on production, the tracers are somewhat separated and a determination of fluid saturations becomes more feasible. The problem with this technique is that it is difficult to determine the time necessary for the tracers to drift. Furthermore, extended residence time in the formation creates other problems, such as gravitational separation of the tracers.

Another way of avoiding the "mirror image" effect is to inject a non-reactive tracer along with a tracer precursor. The injection is followed by a shut-in period during which the precursor is allowed to react to form a tracer. The precursor and corresponding tracer have different partitioning coefficients. During the injection phase, the precursor and non-reactive tracer move away from the well at certain velocities determined by their partitioning coefficients. During the production phase, the non-reactive tracer moves back toward the wellbore at the same rate, but the newly formed tracer, because it has a different partitioning coefficient from that of its precursor, moves at a rate different from that of its precursor. The result is a separation at the wellbore of the two tracers. The problem with this method is that it depends for its success on chemical reactions which are influenced by various factors, such as formation temperature.

The mirror image problem can be completely circumvented by injecting a carrier fluid containing at least two non-reactive tracers having different partition coefficients between the fluid phases into one location in the formation and producing from another. Typically, one well is used to inject the carrier fluid bearing the tracers while another well is used to produce formation fluids. Because different injection and production locations are used, it is unnecessary to rely on fluid drift for the separation of the tracers. Nor is it necessary to use tracer precursors and rely on chemical reactions to produce tracers with different partitioning coefficients. Instead, non-reactive tracers can be used which are chromatographically separated as they pass through the formation and this chromatographic separation is a function of the saturation of the immobile phase.

The basic idea of chromatographic separation was disclosed by Dr. Claude Cooke in U.S. Pat. No. 3,590,923. Cooke injected fluid containing at least two tracers of different partition coefficients. The tracers were chromatographically retarded in their passage through the formation to different extents. The breakthrough of the tracers was detected in another location, and inferences were drawn about the relative proportion of formation fluids.

While the Cooke method was superior to any of those previously used, it suffered from a number of serious drawbacks. First, little guidance was given on the selection of appropriate tracers. Second, the Cooke method used only tracer breakthrough quantities to calculate residual oil saturation. Because of dispersion, stratification, streamline effects and the detection properties of various tracers, it was usually difficult to determine the precise time of breakthrough with great accuracy. Even when breakthrough was determined with considerable accuracy, the effect of using only the breakthrough was that only the residual oil saturation of the most permeable layer was determined. The saturation of other layers in the formation was not determined by this technique. Thus, there still exists a need in the industry for a method to accurately determine the residual oil saturation of a formation, especially a watered-out reservoir.

SUMMARY OF THE INVENTION

The present invention relates to an improved process in which residual oil saturations of a watered-out hydrocarbon-containing formation are determined by injecting a fluid containing at least two properly selected, non-reactive, water soluble tracers into the formation. The tracers have different partition coefficients and are chromatographically retarded in their passage through the formation to differing extents. The presence and amounts of the tracers are detected over extended periods of time at another location. The complete results are an using chromatographic theory or reservoir simulation methods to determine the residual oil saturation for various portions of the formation between the injection and production locations.

The present invention requires selecting appropriate tracers. The tracers used are tritiated or carbon 14 tagged alcohols, such as methanol, ethanol, normal and iso-propanols and various isomers of butanols and pentanols, and tritiated or carbon 14 tagged ketones and alkehydes containing up to 6 carbons. It is preferred that at least one tracer is oil-partitioning while at least one is oil-nonpartitioning.

The tracers are injected into the formation through an injector well. Production is from a well or wells in communication with the injection well. The producers can also be non-producing observation-sampling wells where small but representative samples are obtained with time. Samples are taken of the produced fluids over an extended period of time and are analyzed for the presence and amount of the tracers. The residual oil saturations are calculated according to chromatographic theory using the breakthrough quantities and the production function of the tracers.

BRIEF DESCRIPTION OF THE FIGURE

FIG. 1 is a plot of the specific activity of two tracers as a function of cumulative water production.

FIG. 2 is a plot of tracer production and normalized recoveries in a test well.

FIG. 3 is a plot of the residual oil saturations at all recovery levels in a test well.

FIG. 4 is a plot of the residual oil saturations at all recovery levels in a repeat of the test well.

FIG. 5 is a plot of tracer production and normalized recoveries in a repeat of the test well.

DETAILED DESCRIPTION OF THE INVENTION

SELECTION OF TRACERS

Tracers useful in this method include tritiated or carbon 14 tagged alcohols, ketones and alkehydes. Tritiated alcohols are ordinary alcohols with at least one non-hydroxyl hydrogen replaced by tritium. Carbon 14 tagged alcohols are ordinary alcohols with at least one ordinary carbon atom replaced by carbon 14. These alcohols may contain up to 5 carbons. Tritiated or carbon 14 tagged ketones and aldehydes have at least one non-hydroxyl hydrogen replaced by tritium or have at least one carbon atom replaced by carbon 14, respectively. These ketones and aldehydes may contain up to 6 carbons. Selection of the appropriate tracers is based on their partition coefficient at reservoir conditions. Persons skilled in the art can easily measure the partition coefficients in the laboratory in a cell with live oil, resident brine and the tracers to be tested, at the reservoir pressure and temperature.

DESCRIPTION OF THE METHOD

Conventional interwell tests with non-partitioning water-phase tracers are routinely performed prior to start-up of pilot or commercial enhanced oil recovery projects. These tests can provide useful information on flow distribution, channeling and communication so that strategies can be developed and remedial actions planned before commencing solvent injection. The scope of these tests can be easily and inexpensively expanded by including partitioning tracers along with the nonpartitioning tracers in the interwell tests.

Preferably, the tracers used to measure residual oil saturation include at least one oil-nonpartitioning tracer, typically tritiated or carbon 14 tagged alcohols, such as methanol, ethanol, normal and isopropanols, ketones, such as acetone, aldehydes, such as formaldehyde and acetaldehyde, and water or other oil insoluble inorganic and organic radioactive isotopes. The preferred oil non-partitioning tracer is tritiated methanol. The tracers will also include at least one and possibly more oil-partitioning tracers, typically various isomers of tritiated or carbon 14 tagged alcohols, such as butanols and pentanols, and ketones and aldehydes with 2 to 6 carbons. The preferred oil-partitioning tracer is tritiated n-butanol.

The oil-partitioning tracer should meet the requirement that the value of the parameter K * So/Sw should be within the range of 0.2 to 5.0. That is:

$$0.2 < K^* So/Sw < 5.0$$

where K is the partition coefficient defined as the ratio of the tracer concentration in the oil phase to that in the water phase at equilibrium, So is the oil saturation, and Sw is the water saturation.

If two tracers of different oil partition coefficients are used, instead of one non-partitioning and one partitioning tracer, the method of selecting the two oil-partitioning tracers should be as follows:

$K1* So/Sw < 5.0$ and $0.2 < K2 * So/Sw < 5.0$ and $1.2 < [1+K2*SO/Sw]/(1+K1* So/Sw]$ where K1 and K2 are the partition coefficients for the least oil-partitioning and the most oil-partitioning tracers, respectively.

Produced tracers need to be separated first prior to analysis. Fractional distillation, salt-out and adsorption of high molecular weight tracers on hydrocarbon-coated LC (liquid chromatograph) cartridges are among the most effective methods for separating tracers. After separation, the apparent activities of the tracers can be directly measured by a liquid scintillation counter. Then, with a proper correction for cross-contamination and the tritium exchange that might occur during separation, the true activities of the individual tracers can be evaluated from the apparent activities. In this regard, it is preferred that one tracer is a tritiated compound while another one is a carbon 14 tagged compound so that these two tracers can be detected simultaneously independent of each other using a multichannel liquid scintillation counter without prior separation.

In designing an experiment, production wells adjacent to a water injector would ideally have stable oil to water ratios of less than 5% and produced water composition close to that of the injected water. A mixture of tracers is injected as a spike, a slug or continuously at low concentrations with the brine. Water samples are then routinely collected from surrounding production wells. Production and injection rates of the wells being tested and the surrounding wells should be held as steady as possible throughout the test. The water samples are analyzed for tracer response, from which results residual oil saturation can be determined by the technique described below, or by reservoir simulation.

Data Interpretation

In the preferred method, the oil partitioning tracer moves through the formation slower than the non-partitioning tracer. The response curves for the tracers show a lag in the recovery of the partitioning tracer. To calculate the residual oil saturation, one must select "landmark" events, such as the peak, from the response curves of the tracers. The cumulative water productions for the landmark event are used to calculate Sor as follows:

$$\frac{\text{Partitioning tracer "landmark" production}}{\text{Non-partitioning tracer "landmark" production}} = 1 + \frac{K * Sor}{1 - Sor} \quad (1)$$

where K is the partition coefficient of the partitioning tracer.

When two oil partitioning tracers with different partition coefficients are used, the Sor can be calculated using the following formula:

$$\frac{\text{Most partitioning tracer "landmark" production}}{\text{Least partitioning tracer "landmark" production}} = \frac{1 + \frac{K2 * Sor}{1 - Sor}}{1 + \frac{K1 * Sor}{1 - Sor}} \quad (2)$$

where K1 and K2 are the partition coefficients for the least oil partitioning and the most oil partitioning tracers, respectively.

In applying the above equations, any identifiable production curve "landmark" such as breakthrough, peak or half-height production can be picked for Sor calculation. Cooke's patent, for instance, recommended selecting breakthrough time. Conventional chromatography usually focuses on peak times because of the precision with which they can be detected. Under ideal conditions the Sor values calculated from the various "landmarks" will be identical.

For noisy tracer production curves, there can be significant reading errors in locating the "landmarks". To circumvent this problem, the recovery curve, which practically smooths the noises in the production curve by integration, is used in lieu of the error-prone "landmark" for calculating residual oil saturation. According to the chromatographic transformation theory, it can be shown that equations 1 and 2 also hold for any given recovery R.

$$\frac{\text{partitioning tracer production time at recovery } R}{\text{non-partitioning tracer production time at recovery } R} = 1 + \frac{K*Sor}{1 - Sor} \quad (3)$$

and $$\frac{\text{most partitioning tracer production time at recovery } R}{\text{least partitioning tracer production time at recovery } R} = \frac{1 - Sor + K2*Sor}{1 - Sor + K1*Sor} \quad (4)$$

Cumulative recovery R cannot be calculated if the amount and the assay of the tracers injected are not exactly known. For such a case, instead of actual recovery, normalized recovery which is defined as the cumulative production of a tracer normalized by the cumulative production at the peak (or any other prominent landmarks) can be used in equations (3) and (4) for calculating residual oil saturation.

EXAMPLE 1

Interwell Sor technology was applied at a carbonate reservoir. Injection consisted of 18 GBq (.5 Curie) each of tritiated n-butanol and tritiated methanol. Water production from a well 64 meters away was then sampled periodically and analyzed for tracer activities. Tritiated n-butanol, as the partitioning tracer (i.e., it has some solubility in oil), moved slower than the non-partitioning tritiated methanol. From the separation of the response curves for these tracers, Sor was calculated using equation (1) where K is n-butanol's partition coefficient as measured in the laboratory. "Landmark" production is cumulative water production after tracer injection for some characteristic of the tracer response curve. (Time can be used in place of production in the trivial case of constant production rate.)

FIG. 1 shows specific tracer activities as DPM/ml (disintegrations per minute per milliliter of produced water) as a function of cumulative water production from the time of tracer injection. The production of tritiated n-butanol was clearly delayed as predicted. Two "landmarks", namely the production at the interpolated peak and half-height were chosen for calculation of Sor. The resulting values were found to be 35% for both "landmarks".

As a part of the evaluation program, a sponge core was cut at an observation well drilled between the injector and producer wells and a single well tracer test was carried out on the producer. Values of Sor obtained by each of the three methods are set forth in Table I.

TABLE I

| Method | Sor Value |
| --- | --- |
| Interwell Single-well | 35% |
| Mass Balance | 35% |
| Simulation | 40% |
| Sponge Core | 33% |

EXAMPLE 2

Interwell tracer test was run at another carbonate reservoir using (0.8 Curies) tritiated water as the non-partitioning tracer and (0.5 Curies) tritiated n-butanol and (0.2 Curies) carbon-14 tagged i-amyl alcohol as the two partitioning tracers. Tracer production and normalized recoveries are depicted in the upper and lower graphs respectively in FIG. 2. Using equations (3) and (4), residual oil saturations were calculated at all recovery levels and plotted in FIG. 3. The residual oil saturation was found to be constant at 27% from both partitioning tracers for the whole curve.

The test was repeated 5 months after the first test. Water was injected at high rate between tests. The test results are shown in FIG. 4 and the residual oil saturation vs. normalized recovery plot is shown in FIG. 5. The residual oil saturation was found to be 12% from both partitioning tracers. A theoretical analysis indicated that the low residual oil saturation for the second test is a direct result of mobilization of residual oil at high capillary number during the high rate waterflood.

The principle of the invention, a detailed description of one specific application of the principle, and the best mode in which it is contemplated to apply that principle have been described. It is to be understood that the foregoing is illustrative only and that other means and techniques can be employed without departing from the true scope of the invention defined in the following claims.

What is claimed is:

1. A method for determining residual oil saturation of a watered-out reservoir, comprising:
   (a) selecting at least two tracers from the group consisting of alcohols, ketones, aldehydes, water and oil insoluble inorganic and organic radioactive isotopes such that said tracers are tritiated or carbon 14 tagged and such that the partition coefficient, K1, of a first tracer is lower than the partition coefficient, K2, of a second tracer, and ti K1*So/Sw<5.0 and $$0.2 < K2*So/Sw < 5.0 \text{ and}$$

$$1.2 < \{1+K2*So/Sw\}/\{1+K1*So/Sw\}$$

where Si is oil saturation and Sw is water saturation;
   (b) injecting into an injector well a mixture comprising at least said tracers;
   (c) producing said mixture from a production well in communication with said injection well;
   (d) collecting samples of said produced mixture; and
   (e) analyzing said samples for the presence of said tracers to correlate the presence of said tracers and to determine residual oil saturation.

2. The method of claim 1, wherein one of said tracers is a tritiated or carbon-14 tagged alcohol and said alcohol contains up to 5 carbon atoms.

3. The method of claim 1, wherein one of said tracers is a ketone or aldehyde and said ketone or aldehyde contains up to 6 carbon atoms.

4. The method of claim 1, wherein the first tracer is oil nonpartitioning and is selected from the group consisting of methanol, ethanol, normal and iso-propanol, formaldehyde, acetaldehyde, acetone, water and oil insoluble inorganic, and organic radioactive isotopes such that said first tracer is tritiated or carbon 14 tagged.

5. The method of claim 1, wherein the second tracer is selected from the group consisting of tritiated or carbon 14 tagged butanols, pentanols, and ketones and aldehydes containing from 2 to 6 carbons.

6. The method of claim 1, wherein the first tracer is tritiated methanol and the second tracer is tritiated n-butanol.

7. A method for determining residual oil saturation of a watered-out reservoir, comprising:
   (a) selecting a first tracer which is oil-nonpartitioning from the group consisting of methanol, ethanol, normal and iso-propanol, formaldehyde, acetaldehyde, acetone, water and oil insoluble inorganic and organic radioactive isotopes such that said first tracer is tritiated or carbon 14 tagged;
   (b) selecting a second tracer which is oil partitioning from the group consisting of butanols, pentanols, and ketones and aldehydes containing from 2 to 6 carbon atoms, such that said second tracer is tritiated or carbon 14 tagged;
   (c) injecting into an injector well a mixture comprising at least said first and second tracers;
   (d) producing said mixture from a production well in communication with said injection well;
   (e) collecting samples of said produced mixture; and
   (f) analyzing said samples for the presence of said tracers to correlate the presence of said tracers and to determine residual oil saturation.

8. The method of claim 7, wherein the first tracer is tritiated methanol and the second tracer is tritiated n-butanol.

* * * * *